United States Patent

Baudin

Patent Number: 5,264,615
Date of Patent: Nov. 23, 1993

[54] SCHIFF BASES

[75] Inventor: Josianne Baudin, Annemasse, France

[73] Assignee: Givaudan Corporation, Clifton, N.J.

[21] Appl. No.: 777,297

[22] PCT Filed: Apr. 22, 1991

[86] PCT No.: PCT/EP91/00773

§ 371 Date: Dec. 9, 1991

§ 102(e) Date: Dec. 9, 1991

[87] PCT Pub. No.: WO91/17139

PCT Pub. Date: Nov. 14, 1991

[30] Foreign Application Priority Data

Apr. 27, 1990 [EP] European Pat. Off. ............ 90108028
May 10, 1990 [EP] European Pat. Off. ............ 90810350

[51] Int. Cl.$^5$ .............. C07C 229/38; C07C 229/56; A61K 7/46

[52] U.S. Cl. ..................... 560/35; 512/14; 512/17; 512/18; 514/535

[58] Field of Search ............. 560/35; 514/535; 512/17, 18, 14

[56] References Cited

U.S. PATENT DOCUMENTS

| | | | |
|---|---|---|---|
| 4,806,363 | 2/1989 | Mookherjee et al. | 426/3 |
| 4,853,369 | 8/1989 | Mookherjee et al. | 512/25 |
| 5,084,440 | 1/1992 | Baudin et al. | 512/12 |
| 5,155,095 | 10/1992 | Blanc et al. | 560/35 |

FOREIGN PATENT DOCUMENTS

| | | | |
|---|---|---|---|
| 50-40761 | 4/1975 | Japan | 512/17 |
| 58-35142 | 3/1983 | Japan | 512/17 |
| 60-78951 | 5/1985 | Japan | 512/18 |
| 7802038 | 8/1978 | Netherlands | 512/17 |

OTHER PUBLICATIONS

Mar., *Advanced Organic Chemistry*, 3rd ed., pp. 796–797.
CA 107: 242459b (1987).

Primary Examiner—José G. Dees
Assistant Examiner—B. Frazier
Attorney, Agent, or Firm—Robert F. Tavares; Linda A. Vag

[57] ABSTRACT

Schiff bases having the formula

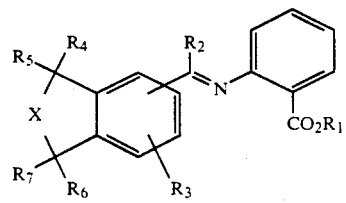

I wherein
$R^1$ signifies $CH_3$, $C_2H_5$
$R^2$ signifies H, $CH_3$
$R^3$ signifies H, $C_{1-4}$-alkyl
$R^4$, $R^5$, $R^6$, $R^7$ signify H, $CH_3$, $C_2H_5$, $CH_2CH_2CH_3$, $CH(CH_3)_2$,
X signifies methylene, ethylidene, propylidene, ethylene, propylene, 2,3-butylidene, total number of carbon atoms of $R^4$, $R^5$, $R^6$, $R^7$, $\leq 6$ are novel odorants.

15 Claims, No Drawings

SCHIFF BASES

The invention relates to novel odorants, namely Schiff bases.

In particular, the invention is concerned with the compounds of the formula

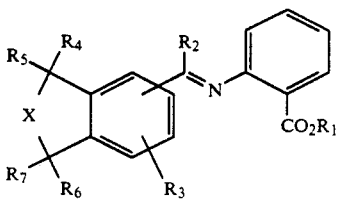
I wherein
- $R^1$ signifies $CH_3$, $C_2H_5$
- $R^2$ signifies H, $CH_3$
- $R^3$ signifies H, $C_{1-4}$-alkyl
- $R^4$, $R^5$, $R^6$,
- $R^7$ signify H, $CH_3$, $C_2H_5$, $CH_2CH_2CH_3$, $CH(CH_3)_2$,
- X signifies methylene, ethylidene, propylidene, ethylene, propylene, 2,3-butylidene. total number of carbon atoms of $R^4$, $R^5$, $R^6$, $R^7$, $\leq 6$ Accordingly, tetralins and indanes are embraced by formula I.

The compounds of formula I are distinguished by very natural notes in the direction of musk. Worthy of mentioning is in particular a frequent combination of musky and flowery notes, this combination of notes being of particular interest because of the resulting powerful body notes. Concerning the flowery notes, the orange blossom and tuberose aspects may in particular be mentioned.

They exhibit good substantivity, especially in fabric softeners and detergents.

They are not only suited in odorant compositions of the flowery, but also of many other types, especially those suited in the field of the luxury perfumery.

The compounds of formula I are obtained as the essential reaction products of a process comprising reacting a carbonyl compound of formula

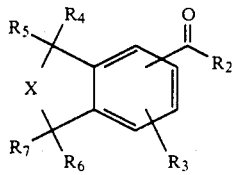
II with an alkyl anthranilate of formula

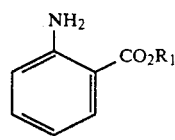
III

The convenient process parameters are as follows:
Temperature: ca. 30° C. to 150° C.
Pressure: from ca. 1 atm. down to 20 mmHg
Solvents: not necessary
Molecular proportions
of II/III: ca. 1:2 to ca. 2:1, with ca. 1:1 being preferred Catalysts: acids, e.g., organic acids such as p-toluene sulfonic acid, Lewis acids, such as $BF_3$, etc., molecular sieves of the acid type Working up: (concentration by) distillation off starting materials under reduced pressure, then crystallization of the residue; or utilization of the residue as such. The crystallization is effected using solvents such as heptane or ethanol, etc.

The carbonyls II can also be used in the form of their acetals of ketals, namely the derivatives of the formula

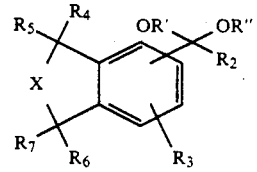
II′ see for example EP 0379981 (A₁), formula I for the definition of the radicals and the preparation of such derivatives.

The novel Schiff bases combine with numerous known odorant ingredients of natural or synthetic origin, whereby the range of the natural raw substances can embrace not only readily-volatile, but also moderately-volatile and slightly-volatile components and that of the synthetics can embrace representatives from practically all classes of substances, as will be evident from the following compilation:

Natural products, such as tree moss absolute, basil oil, citrus fruit oils (such as bergamot oil, mandarin oil, etc.), mastrix absolute, myrtle oil, palmarosa oil, patchouli oil, petitgrain oil Paraguay, wormwood oil, alcohols, such as farnesol, geraniol, linalool, nerol, phenylethyl alcohol, rhodinol, cinnamic alcohol, aldehydes, such as citral, Helional ®, α-hexylcinnamaldehyde, hydroxycitronellal, Lilial ®(p-tert-.butyl-α-methyl-dihydrocinnamaldehyde), methylnonylacetaldehyde, ketones, such as allylionone, α-ionone, β-ionone, isoraldein (isomethyl-α-ionone), methylionone, esters, such as allyl phenoxyacetate, benzyl salicylate, cinnamyl propionate, citronellyl acetate, citronellyl ethoxolate (citronellyl) . O—CO—CO. OC₂H₅), decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, etc., lactones, such as γ-undecalactone.

various components often used in perfumary, such as musk ketone, indole, p-menthane-8-thiol-3-one, methyleugenol.

The Schiff bases can be used in wide limits which can range in compositions, for example, from about 0.1 (detergents)-about 20% (alcoholic solutions), without these values being, however, limiting values, as the experienced perfumer can also achieve effects with even lower concentrations or can synthesize novel complexes with even higher amounts. The preferred concentrations range between about 1 and about 10%. The compositions manufactured with I can be used for all kinds of perfumed consumer goods (eau de cologne, each de toilette, extracts, lotions, creams, shampoos, soaps, salves, powders, toothpastes, mouth washes, deodorants, detergents, fabric conditioners, tobacco, etc.).

The Schiff bases can accordingly be used in the manufacture of compositions and-as the above compilation shows-using a wide range of known odorants or odorant mixtures. In the manufacture of such compositions the known odorants referred to above can be used according to methods known to the perfumer such as e.g. from W. A. Poucher, Perfumes, Cosmetics and Soaps 2, 7th Edition, Chapman and Hall, London, 1974.

EXAMPLES

1. Method A

Into a three necked reaction flask equipped with a stirrer, a thermometer, a water trap and a condenser, 0.5 moles of aldehyde or ketone II is added to 0.5 moles of alkyl anthranilate III.

The vacuum is adjusted to 100 mmHg and the reactor is heated slowly to 100° C., then maintained at 120°-130° C. until the reaction does not progress any more. (The reaction is monitored by GC and $^1$H NMR). The reaction mass may be used as that or it is distilled under vacuo to remove any starting materials still present.

The following products have been prepared according to this method A.

employing Methyl anthranilate (MA), or ethyl anthranilate (EA)

1)

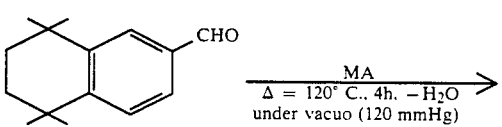

The reaction mass is used crude without any purification. The yellow liquid mixture contains 30% of aldehyde, 5% of methyl anthranilate, and 65% of the Schiff Base (methyl-N-[(1,1,4,4-tetramethyl-tetralin-6-yl)methylidene]-anthranilate). Confirmation by GC analysis (conditions: 25 meters×0.32 mm, OV (stationary phase) 101 programmed at 140°-220° C. at 4° C. per minute); in agreement with $^1$H NMR (200 MHz): 9.96 ppm, s; 3.88 ppm, s; 8.23 ppm, s; 3.84 ppm, s. Odour: honey-like, "oranger" flower (orange blossom), musky, powerful and soft.

2)

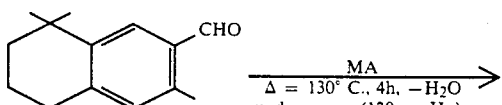

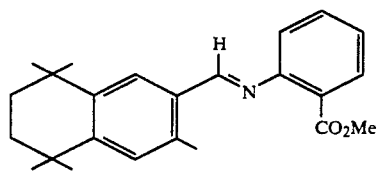

The reaction mass, a yellow liquid contains 30% of aldehyde, 10% of methyl anthranilate, and 60% of the Schiff base (methyl-N-[(1,1,4,4,7-pentamethyl-tetralin-6-yl)methylidene]-anthranilate).

$^1$H NMR (200 MHz): 10.2 ppm, s; 3.88 ppm, s; 8.45 ppm, s; 3.86 ppm, s.

Odour: powdery, polycyclic musk-like, floral (oranger flower).

3)

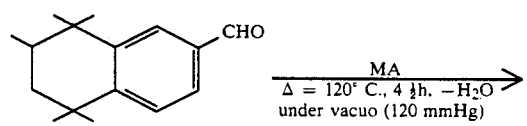

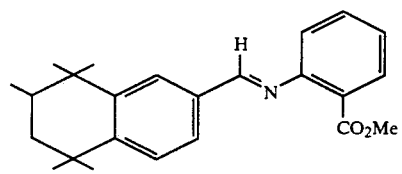

The crude product is crystallized with heptane as solvent and gives after filtration a white solid (mp 63°-73° C.) containing: 37% of aldehyde, 15% of methyl anthranilate, and 48% of the Schiff base (methyl-N-[(1,1,3, 4,4-pentamethyl-tetralin-6-yl)methylidene]-anthranilate.

$^1$H NMR (400 MHz): 9.96 ppm, s; 3.84 ppm, s; 5.71 ppm,
  broad s; 8.24 ppm, s; 3.87 ppm, s.

Odour: flowery, musky, woody, oranger.

4)

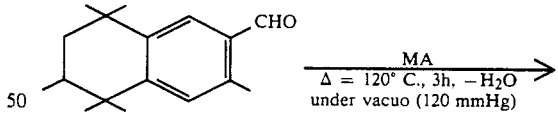

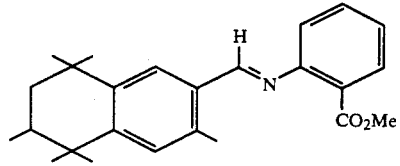

The reaction mass is a yellow liquid containing: 40% of aldehyde, 10% of methyl anthranilate, and 50% of the Schiff base (methyl-N-[(1,1,2,4,4,7-hexamethyl-tetralin -6-yl)methylidene]-anthranilate).

$^1$H NMR (200 MHz): 10.2 ppm, s; 8.50 ppm, s; 3.85 ppm, s; 3.88 ppm, s.

Odour: musky, powdery, floral (oranger flower).

5)

5

-continued

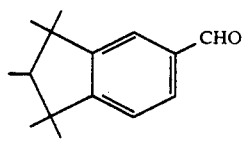

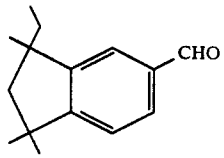

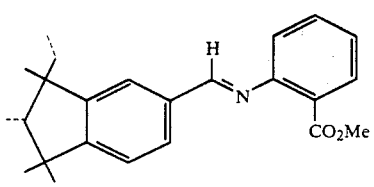

The reaction mass is a yellow liquid containing: 15% of aldehyde, 10% of methyl anthranilate, and 75% of the Schiff base (methyl-N-[(1,1,2,3,3-pentamethyl-indan-5-yl)methylidene]-anthranilate and methyl-N-[(3-ethyl-1,1,3-trimethylindan-5-yl)methylidene]-anthranilate).

$^1$H NMR (200 MHz): 9.98 ppm, 2s; 3.87 ppm, s; 8.27 ppm, s; 3.84 ppm, s.

Odour: musky, floral (oranger flower).

6)

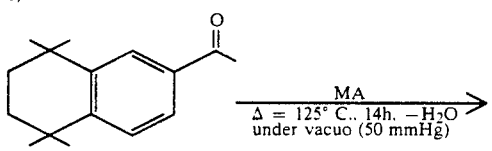

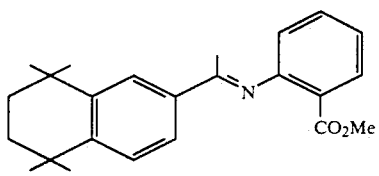

The reaction mass is distilled under vacuo (0.05 mmHg) to remove the starting material and the residue is a green liquid containing 35% of aldehyde, and 65% of the Schiff base (methyl-N-[(1,1,4,4-tetramethyl-tetralin-6-yl)methyl-methylidene]-anthranilate).

$^1$H NMR (200 MHz): 2.57 ppm, s; 2.15 ppm, s; 3.78 ppm, s. Odour: flowery (oranger flower)

7)

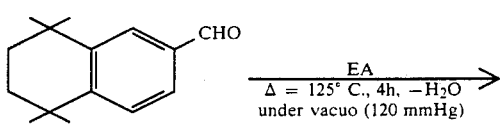

6

-continued

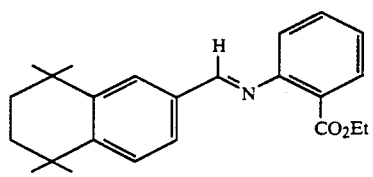

The reaction mass is a yellow liquid containing: 25% of aldehyde, 5% of ethyl anthranilate, and 70% of Schiff base (ethyl-N-[(1,1,4,4-tetramethyl-tetralin-6-yl)methylidene]-anthranilate).

$^1$H NMR (200 MHz): 9.95 ppm, s; 4.29 ppm, quadruplet; 8.22 ppm, s.

Odour: honey-like, oranger-flower, musky.

8)

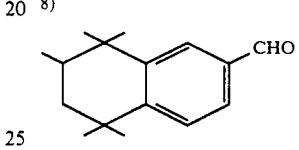

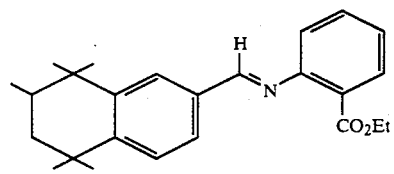

The reaction mass is crystallized out of heptane and gives a white solid mixture (mp 50°-60° C.) containing: 20% of aldehyde, 5% of ethyl anthranilate, and 75% of the Schiff base (ethyl-N-[1,1,3,4,4-pentamethyl-tetralin-6-yl)methylidene]-anthranilate).

$^1$H NMR (200 MHz): 9.95 ppm, s; 5.7 ppm, broad s; 8.24 ppm, s; 4.3 ppm, quadruplet.

Odour: vanilla-like, slightly musky.

2. Method B

About 40 g of molecular sieve (Linde 5 A) are added to 0.10 moles of ketone and 0.12 moles of alkyl anthranilate in 40 ml of toluene. The reaction mixture is shaken between 20° and 80° C. until the formation of ketimine does not progress any more. The reaction is monitored by GC and $^1$H NMR (200 MHz).

The mixture is then seperated from the molecular sieves and the latter are washed with toluene. Solvent is removed from the filtrate by rotary evaporation and the crude is purified by vacuum distillation or crystallization.

The following products have been prepared according to this method B.

9)

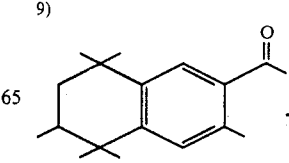

-continued

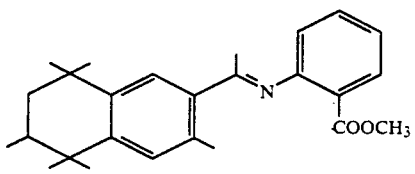

The crude product is distilled under vacuo (0.5 mmHg) to remove the starting material and the residue is crystallized out of ethanol. By this way a pure white ketimine is obtained (methyl-N-[(1,1,2,4,4,7-hexamehyl-tetralin-6-yl)methyl-methylidene]-anthranilate), mp 111°-112° C., GC 100%, $^1$H NMR (400 MHz): 2.5 ppm, s; 2.12 ppm, s; 3.84 ppm, s. Odour: floral (oranger flower), fresh.

10)

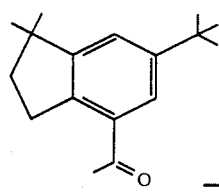

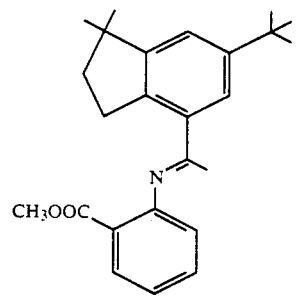

A vacuum distillation provides a pure ketimine (methyl-N-[(1,1-dimethyl-6-tert-butyl-indan-4-yl)methyl-methylidene]-anthranilate), bp 150° C., under vacuo (0.2 mmHg) GC 100%, $^1$H NMR (400 MHz): 2.16 ppm, s; 3.81 ppm, s. Odour: Yara-yara (β-naphthol methyl ether, i.e. intensely sweet, orange blossom-acacia like).

3. Method C

Onto a reaction flask equipped with a stirrer, a thermometer, an alcohol trap and a condenser, 0.1 mole of ketal or acetal II' of the carbonyl compound II is added to 0.05 mole (generally: from ca. 0.05 mole to ca. 0.1 mole) of alkyl anthranilate III. The vacuum is adjusted to 120 mm Hg and the reactor is heated slowly to 100° C., then maintained at 100°-110° C. until the reaction does not progress anymore. (The reaction is monitored by GC and $^1$H NMR). The reaction mass is then cooled and may be used as such without any purification step or it is distilled under vacuo to remove any starting materials still present. The following products have been prepared according to this method C, employing methyl anthranilate (M.A.)

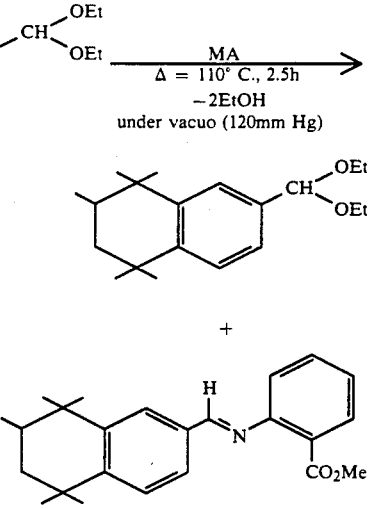

The reaction mass is a yellow liquid containing: 55% of Schiff base (methyl-N-[(1,1,3,4,4-pentamethyl-tetralin -6-yl)-methylidene]-anthranilate), 44% of 6-(formyl-diethyl-acetal)-1,1,3,4,4-pentamethyl-tretralin and 1% of 6-formyl-1,1,3,4,4-pentamethyl-tetralin.

Confirmation: by GC analysis (conditions: 25 meters×0.32 mm, OV 101 (stationary phase) programmed at 140°-220° C. at 4° C. per minute); the structure is in agreement with $^1$H NMR (80 MHz): 9.96 ppm, s; 5.44 ppm, s; 3.77 ppm, s; 8.20 ppm, s;

Odour: Flowery, musky, slightly woody.

EXAMPLE 11

| Odorant composition | parts by weight | parts by weight |
| --- | --- | --- |
| Cedar wood oil | 50.00 | 50.00 |
| Benzyl acetate | 80.00 | 80.00 |
| Geraniol extra | 50.00 | 50.00 |
| Isoraldeine (methyl ionone) | 30.00 | 30.00 |
| Phenylethyl alcohol | 120.00 | 120.00 |
| Hydroxycitronellal | 120.00 | 120.00 |
| Benzyl salicylate | 70.00 | 70.00 |
| Hedione (methyldihydrojasmonate) | 150.00 | 150.00 |
| Hexyl cinnamic aldehyde | 200.00 | 200.00 |
| Cetonial (Helional) | 15.00 | 15.00 |
| cis-Hexenyl salicylate | 15.00 | 15.00 |
| LRG 1201 Evernyl (Benzoic acid 3,4-dihydroxy-3,6-dimethyl-methyl ester) | 5.00 | 5.00 |
| Clove oil | 8.00 | 8.00 |
| Heliotropine crist. | 8.00 | 8.00 |
| Mandarine oil | 15.00 | 15.00 |
| Phenyl acetaldehyde | 2.00 | 2.00 |
| n-Undecylenaldehyde (1% in Carbitol) | 2.00 | 2.00 |
| Methyl-N-[(1,1,3,4,4-penta-methyl-tetralin-6-yl)-methylidene]-anthranilate/ 7-Formyl-1,1,2,4,4-penta-methyl-tetralin | | 60.00 |
| Dipropylene glycol | 60.00 | |

In this white flower accord, in particular suited for Eaux de toilette, the multifacet odour (musk, orange blossom) contributes to the esthetics of the perfume, in particular in as fer as the musk note is concerned.

EXAMPLE 12

| Odorant composition | parts by weight | parts by weight |
| --- | --- | --- |
| Allyl cyclohexyl propionate | 1.00 | 1.00 |
| Styrallyl acetate | 2.00 | 2.00 |
| Isoeugenol | 2.00 | 2.00 |
| Geranium oxide 10% | 5.00 | 5.00 |
| Verdyl acetate | 20.00 | 20.00 |
| Dimetol | 20.00 | 20.00 |
| Petitgrain essence Paraguay | 20.00 | 20.00 |
| Linalool | 30.00 | 30.00 |
| Benzyl acetate | 100.00 | 100.00 |
| Geranyl acetate | 100.00 | 100.00 |
| Phenylethyl alcohol | 150.00 | 150.00 |
| Hexyl cinnamic aldehyde | 200.00 | 200.00 |
| Beramote essence | 300.00 | 300.00 |
| Methyl-N-[(1,1,3,4,4-pentamethyl-tetralin-6-yl)-methylidene]-anthranilate/ | | 50.00 |
| 7-Formyl-1,1,2,4,4-pentamethyl-tetralin | | |
| Diprolene glycol | 50.00 | |

The above formula is in particular suited for shampoos, and the compound of example 3 enhances in particular the body notes of the formulation.

I claim:

1. A Schiff base having the formula

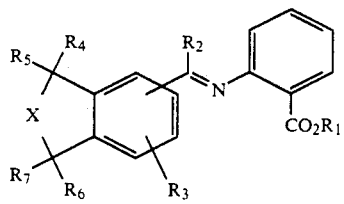

wherein:
R$^1$ signifies CH$_3$, C$_2$H$_5$,
R$^2$ signifies H, CH$_3$,
R$^3$ signifies H, C$_{1-4}$-alkyl,
R$^4$, R$^5$, R$^6$, R$^7$ signify H, CH$_3$, C$_2$H$_5$, CH$_2$CH$_2$CH$_3$, CH(CH$_3$)$_2$,
X signifies methylene, ethylidene, propylidene, ethylene, propylene, 2,3-butylidene, and,
the total number of carbon atoms of R$^4$, R$^5$, R$^6$, R$^7$, is ≦6.

2. The Schiff base in accordance with claim 1 which is Methyl-N-((1,1,3,4,4-pentamethyl-tetralin-6-yl)-methylidene)-anthranilate.

3. The Schiff base in accordance with claim 1 which is Methyl-N-((1,1,2,4,4,7-hexamethyl-tetralin-6-yl)-methylidene)-anthranilate.

4. The Schiff base in accordance with claim 1 which is Methyl-N-((1,1,2,4,4,7-hexamethyl-tetralin-6-yl)-methyl-methylidene)-anthranilate.

5. The Schiff base in accordance with claim 1 which is Methyl-N-((1,1-dimethyl-6-tert-butyl-indan-4-yl)-methyl-methylidene)-anthranilate.

6. An odorant composition which comprises an olfactorily effective amount of a Schiff base having the formula

I wherein:
R$^1$ signifies CH$_3$, C$_2$H$_5$,
R$^2$ signifies H, CH$_3$,
R$^3$ signifies H, C$_{1-4}$-alkyl,
R$^4$, R$^5$, R$^6$, R$^7$ signify H, CH$_3$, C$_2$H$_5$, CH$_2$CH$_2$CH$_3$, CH(CH$_3$)$_2$,
X signifies methylene, ethylidene, propylidene, ethylene, propylene, 2,3-butylidene, and, the total number of carbon atoms of R$^4$, R$^5$, R$^6$, R$^7$, is ≦6.
and at least one other olfactive agent.

7. An odorant composition in accordance with claim 6 wherein the Schiff base is Methyl-N-((1,1,3,4,4-pentamethyl-tetralin-6-yl)-methylidene)-anthranilate.

8. An odorant composition in accordance with claim 6 wherein the Schiff base is Methyl-N-((1,1,2,4,4,7-hexamethyl-tetralin-6-yl)-methylidene)anthranilate.

9. An odorant composition in accordance with claim 6 wherein the Schiff base is Methyl-N-((1,1,2,4,4,7-hexamethyl-tetralin-6-yl)-methylmethylidene)-anthranilate.

10. An odorant composition in accordance with claim 6 wherein the Schiff base is Methyl-N-((1,1-dimethyl-6-tert-butyl-indan-4-yl)-methyl-methylidene)-anthranilate.

11. A method for improving the odor of an odorant composition which comprises adding thereto an olfactorily effective amount of a Schiff base having the formula

I wherein:
R$^1$ signifies CH$_3$, C$_2$H$_5$,
R$^2$ signifies H, CH$_3$,
R$^3$ signifies H, C$_{1-4}$-alkyl,
R$^4$, R$^5$, R$^6$, R$^7$ signify H, CH$_3$, C$_2$H$_5$, CH$_2$CH$_2$CH$_3$, CH(CH$_3$)$_2$,
X signifies methylene, ethylidene, propylidene, ethylene, propylene, 2,3-butylidene, and,
the total number of carbon atoms of R$^4$, R$^5$, R$^6$, R$^7$, is ≦6.

12. A method in accordance with claim 11 wherein the Schiff base is Methyl-N-((1,1,3,4,4-pentamethyl-tetralin-6-yl)-methylidene)anthranilate.

13. A method in accordance with claim 11 wherein the Schiff base is Methyl-N-((1,1,2,4,4,7-hexamethyl-tetralin-6-yl)-methylidene)anthranilate.

14. A method in accordance with claim 11 wherein the Schiff base is Methyl-N-((1,1,2,4,4,7-hexamethyl-tetralin-6-yl)-methyl-methylidene)anthranilate.

15. A method in accordance with claim 11 wherein the Schiff base is Methyl-N-((1,1-dimethyl-6-tert-butyl-indan-4-yl)-methyl-methylidene)anthranilate.

* * * * *